United States Patent [19]

Bagley et al.

[11] Patent Number: 5,242,512
[45] Date of Patent: Sep. 7, 1993

[54] METHOD AND APPARATUS FOR RELIEVING RESIDUAL STRESSES

[75] Inventors: William H. Bagley, Bloomfield; James R. Rosbe, Ann Arbor; Douglas G. Wilson, Mt. Clemens, all of Mich.

[73] Assignee: Alloying Surfaces, Inc.

[21] Appl. No.: 851,996

[22] Filed: Mar. 13, 1992

[51] Int. Cl.⁵ ............................................. C21D 11/00
[52] U.S. Cl. ..................................... 148/558; 266/90
[58] Field of Search ................... 148/558; 73/579, 662; 266/78, 80, 90

[56] References Cited

U.S. PATENT DOCUMENTS

| | | | |
|---|---|---|---|
| 2,848,775 | 8/1958 | Ettenreich | 148/558 |
| 3,622,404 | 11/1971 | Thompson | 148/558 |
| 3,677,831 | 7/1972 | Pezaris | 148/558 |
| 3,741,820 | 6/1973 | Hebel, Jr. et al. | 148/558 |
| 3,786,448 | 1/1974 | Batcher et al. | 340/174 PW |
| 4,381,673 | 5/1983 | Klauba et al. | 73/579 |
| 4,386,727 | 6/1983 | Unde | 228/102 |
| 4,446,733 | 5/1984 | Okubo | 73/579 |
| 4,718,473 | 1/1988 | Musschoot | 148/558 |
| 4,823,599 | 4/1989 | Schneider | 148/558 |
| 4,968,359 | 11/1990 | Hebel, Jr. et al. | 148/558 |

OTHER PUBLICATIONS

"Industrial Profile: Bonal Technologies, Inc.", *Die Cast Management*, Oct., 1991.
"The Computation of the Discrete Fourier Transform and some of its Applications", *Digital Signal Processing: Theory, Design and Implementation*, Robert E. Krieger Publishing Co., Malabar, Florida, Dec. 1985.

*Primary Examiner*—Scott Kastler
*Attorney, Agent, or Firm*—Harness, Dickey & Pierce

[57] ABSTRACT

An apparatus for relieving residual stresses and stabilizing modal behavior in a workpiece, and/or analyzing change in modal behavior of a workpiece to detect buildup of residual stresses. The apparatus includes an exciter for vibrating the workpiece. In addition, the apparatus further includes a computer for varying the frequency at which the workpiece is vibrated in response to the fast fourier transform of the frequency response of the workpiece.

29 Claims, 4 Drawing Sheets

METHOD AND APPARATUS FOR RELIEVING RESIDUAL STRESSES

BACKGROUND OF THE INVENTION

1. Field of the Invention

The present invention relates generally to analyzing the modal behavior of materials for the purpose of detecting the presence or absence of residual stresses, and more particularly to a method and apparatus for relieving residual stresses in a workpiece by vibrating the workpiece.

2. Description of Related Art

Metal working procedures such as forging, casting, welding, machining and the like introduce residual stresses into workpieces. Release of residual stresses, often described as creep or lattice slip, occurs naturally over time as a workpiece ages, in a process known as stress-directed atomic diffusion, whereby natural tensile and compressive stresses equalize and residual stresses are released. If sufficient time is not allowed for such diffusion to occur in a workpiece, these residual stresses can result in premature failure of the workpiece, an increased tendency of the workpiece to warp or be subject to heat-checking, as well as an increase in the rate of corrosion of the workpiece. Accordingly, various procedures have been used to relieve residual stresses. Such procedures include hot working, step aging, precipitation aging, over-aging, quench aging, progressive aging, heat treatment, cryogenics, cold working operations such as strain aging, shot-peening, and alternating magnetic field excitation. While these techniques have been known in the art, all are fraught with one or more drawbacks including, but not limited to, the cost of equipment and operation, the size of equipment, and their effectiveness in relieving residual stresses. In addition, these techniques generally do not include as an inherent part of their method the ability to verify effective release of residual stresses. Also, in all these methods, comparative measurement of the actual properties of workpieces prior to and after treatment has hitherto been generally limited to costly destructive testing, surface-limited and non-conclusive x-ray diffraction or magnetoelastic surface analysis techniques, or empirical observation of dimensional or other changes (or the lack thereof) during machining or in use.

It is also known that the application of a cyclic vibrational force to a workpiece also relieves residual stresses. Such a method for relieving stress in a workpiece by vibration is described in U.S. Pat. No. 4,968,359. The method described in this reference involves relieving stress by initially applying a vibrational force over a test frequency range, monitoring the dampening effects, identifying a plurality of orders of harmonic vibration absorption peaks, and then applying a vibrating force at a fixed frequency corresponding to a sub-harmonic frequency of one of the harmonic peaks. Another method for relieving stress is described in U.S. Pat. No. 3,741,820 which also involves the vibration of the workpiece at a fixed frequency. Another method for relieving stresses by applying vibrational force is described in U.S. Pat. No. 4,381,673 which involves vibrating at fixed resonant frequencies.

While prior art techniques for relieving stress by applying vibrational forces have generally proven effective, they also have several disadvantages. For example, prior techniques generally do not vary the frequency of the vibration in response to changes in the frequency response of the workpiece as residual stresses are relieved. In addition, such methods heretofore have relied exclusively on measurement of the frequency response of the workpiece by means of a ramp-up of vibrational energy introduced into the workpiece with a series-wound motor-driven exciter. If precise motor speed control is not maintained, these methods and apparati may be inaccurate, causing someone not well-schooled in the art to be misled by false frequency locations caused by operating temperature variations in the exciter motor.

SUMMARY OF THE INVENTION

Accordingly, it is the primary object of the present invention to provide a method and apparatus for relieving residual stresses in a workpiece by vibrating the workpiece. A related object of the present invention is to provide a method and apparatus for relieving residual stresses in a workpiece by vibrating the workpiece at a frequency which varies in response to the frequency response of the workpiece.

Another object of the present invention is to provide a method and apparatus for relieving residual stresses in a workpiece in which the desired amount of stress relief can be achieved relatively rapidly.

An additional object of the present invention is to provide a method and apparatus for relieving residual stresses and changing the modal behavior in a workpiece so as to reduce the possibility of premature failure of the workpiece, reduce the tendency of the workpiece to warp or be subject to heat-checking, as well as reduce the rate of corrosion of the workpiece.

A further object of the present invention is to provide a method and apparatus for verifying the effectiveness of residual stress relief, and for comparing the modal behavior of a workpiece before and after it has been in use or had applied to it any process that may cause residual stresses to build up in it.

These and other objects of the present invention are achieved by providing an apparatus for relieving residual stress in a workpiece which comprises an exciter for inducing mechanical vibration in the workpiece. In addition, the apparatus further comprises an accelerometer for measuring the frequency response of the workpiece. The apparatus also comprises a control unit operable to vary the frequency of the vibration generated by the exciter in response to the fast fourier transform of the output of the accelerometer.

The present invention also achieves the objects and advantages stated above by providing a method for relieving residual stresses in a workpiece by vibrating the workpiece. The method comprises the step of initially attaching an exciter to the workpiece which is able to generate mechanical vibration. The frequency of the vibration generated by the exciter is then varied in response to the frequency response of the workpiece.

BRIEF DESCRIPTION OF THE DRAWINGS

Various advantages of the present invention will become apparent to one skilled in the art upon reading the following specification and by reference to the following drawings in which.

DETAILED DESCRIPTION OF THE PREFERRED EMBODIMENT

Figure 1:
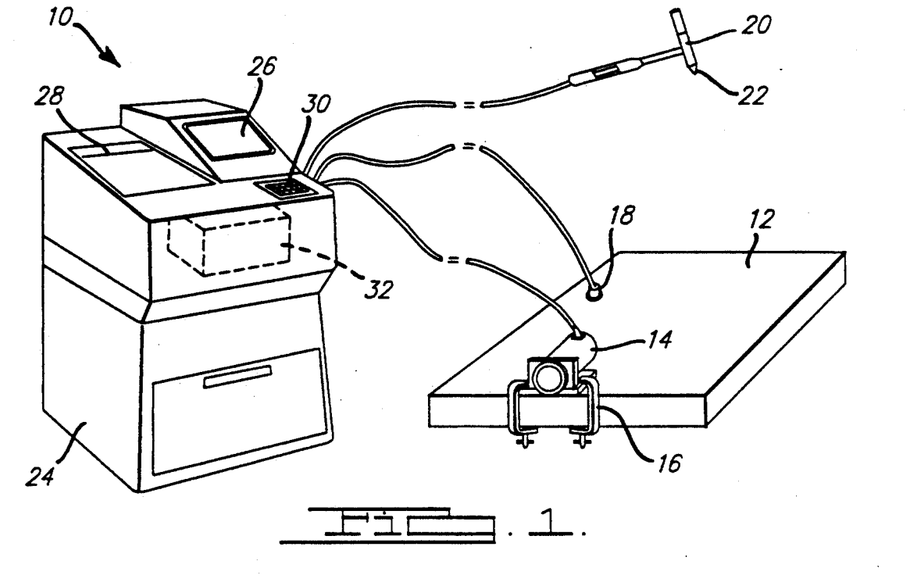
FIG. 1 is the diagrammatical representation of the apparatus for relieving residual stresses according to the preferred embodiment of the present invention as shown in operative association with a workpiece.

Referring to FIG. 1, the apparatus 10 for relieving residual stresses in a workpiece 12 is shown according to the preferred embodiment of the present invention. The workpiece 12 initially has residual stresses which have been generated during the formation of the workpiece 12. If the residual stresses in the workpiece 12 are not relieved, the workpiece 12 will have an increased tendency to warp and corrode, as well as have an increased probability that the workpiece 12 will be subject to heat-checking and premature failure. The apparatus 10 is used to relieve these residual stresses by the application of vibrating force to the workpiece 12. While the workpiece 12 may be a component of an automobile, it will be appreciated that other suitable workpieces may also be used. In addition, while the workpiece 12 may be formed from metal, the workpiece 12 may also be formed of other materials which are susceptible to being stress relieved by the use of mechanical vibration such as ceramics and composite materials.

To provide means for vibrating the workpiece 12, the apparatus 10 comprises an exciter 14. The exciter 14 is removably secured to the workpiece 12 and is used to apply mechanical vibration to the workpiece 12. The exciter 14 includes a variable speed drive which permits frequency of the vibration delivered to the workpiece 12 to be varied. The variable speed drive may include a series electric motor of the type having an armature and field windings connected in series, the speed of which can be controlled by varying the current to the motor. While a clamp 16 may be used to detachably secure the exciter 14 to the workpiece 12, other suitable means may be used.

To provide means for collecting information regarding the frequency response of the workpiece 12, the apparatus 10 further comprises an accelerometer 18. The accelerometer 18 is adapted to be removably secured to the workpiece 12 at a point displaced from the exciter 14. The accelerometer 18 is able to generate an electrical signal in response to the vibrational acceleration of the workpiece 12 caused by the vibrational force delivered to the workpiece 12 by the exciter 10. By analyzing the output from the accelerometer 18 in the manner described below, the frequency response of the workpiece 12 to the vibrational force generated by the exciter 14 can be determined.

To establish the initial frequency at which the workpiece 12 is to be vibrated by the exciter 14, the apparatus further comprises an impact hammer 20. The impact hammer 20 is used to initially perform an impact test on the workpiece 12 in which the workpiece 12 is struck preferably four times with the impact hammer 20 and the frequency response of the workpiece 12 determined as a result of each impact. As more fully discussed below, the frequency response of the workpiece 12 to the impact test allows the apparatus 10 to generate the frequency response function of the workpiece 12. The impact hammer 20 includes a load cell 22 which is used for generating a signal which is indicative of the force applied to the workpiece 12 by the impact hammer 20 during the impact test. The output from the load cell 22 is used to normalize the frequency response of the workpiece 12 each time the workpiece 12 is struck so that the frequency response of the workpiece is independent of the force applied by the impact hammer 20. An alternate means to generate the frequency response function of the workpiece 12 would be the use of a random noise electrodynamic, servohydraulic, or pneumatic exciter in place of the impact hammer with load cell. In addition, the impact hammer 20 may electrically communicate with the control unit described below either by cable, infrared, optical or by radio.

To provide means for varying the frequency at which the workpiece 12 is vibrated, the apparatus 10 further comprises a control unit 24. The control unit 24 receives the output from the accelerometer 18 and the load cell 22 and uses this information to control the exciter 14. In this regard, the control unit 24 includes a multi-channel signal conditioning circuit (not shown) which receives the output from the accelerometer 18 as well as the load cell 22 and amplifies the output prior to delivery to an analog-digital converter (not shown). The control unit 24 further includes a monitor 26 which is used to visually display various graphs which are discussed below, as well as a printer 28 which is used to provide hard copies of these graphs. The control unit 24 also has a key pad 30 which is used by the operator to control the operation of the control unit 24. In addition, the control unit 24 further includes a frequency control loop circuit which is used for generating the proper voltage levels for driving the exciter 14.

Figure 2:
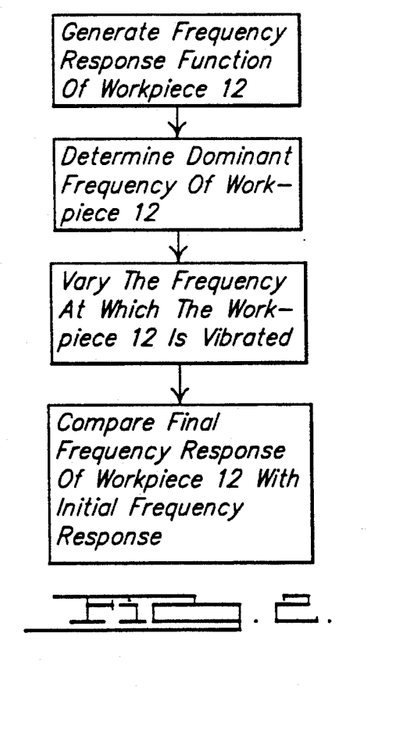
FIG. 2 is a diagrammatic illustration of the operations performed by the computer which is included within the apparatus shown in FIG. 1.

The control unit 24 further comprises a computer 32. The computer 32 is able to use the outputs from the accelerometer 18 and the load cell 22 to control the frequency at which the exciter 14 vibrates the workpiece 12 by performing the four operations which are illustrated in FIG. 2. These operations are (1) generating the frequency response function of the workpiece 12, (2) determining the critical resonant peak frequency of the workpiece 12, (3) varying the frequency at which the workpiece 12 is vibrated and (4) comparing the final frequency response of the workpiece 12 with the initial frequency response. Each of these operations will be discussed below.

1. Generating the Frequency Response Function of the Workpiece

As shown in FIG. 2, the first operation performed by the computer 32 is to generate the frequency response function of the workpiece 12. In this regard, the computer 32 is able to record the output of the load cell 22 as well as the accelerometer 18 in response to an impact test performed on the workpiece 12 so as to generate the frequency response function. The computer 32 then causes the exciter 14 to perform (as described below) a controlled ramp-up of vibrational amplitude at a constant rate from zero frequency to a predetermined maximum frequency and a controlled ramp-down at a constant rate to zero frequency to enable the computer 32 to examine the resonance frequencies of the workpiece 12.

Figure 3A:
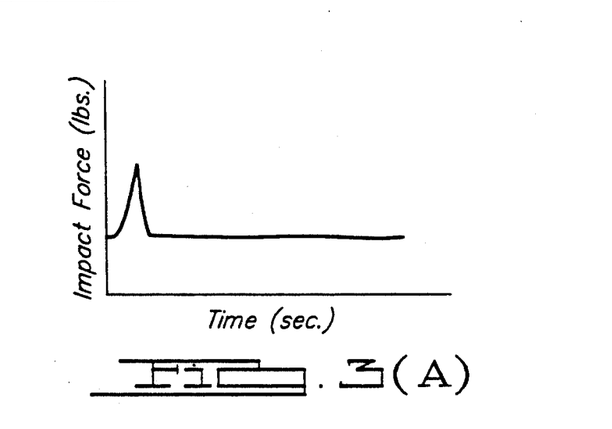
FIG. 3(A) illustrates a graph generated by the apparatus shown in FIG. 1 depicting the impact force applied to the workpiece during an impact test as a function of time.
Figure 3B:
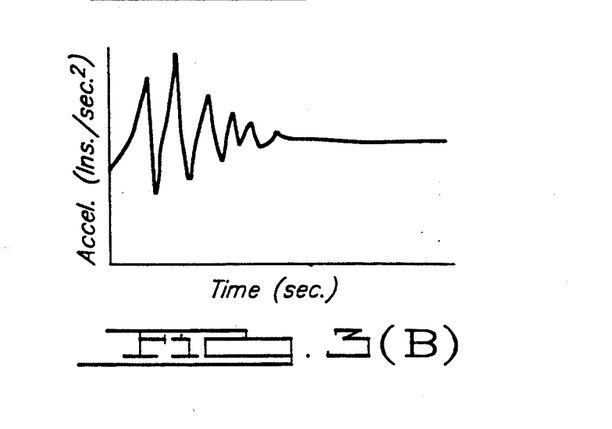
FIG. 3(B) illustrates a graph generated by the apparatus shown in FIG. 1 depicting the acceleration of the workpiece as a function of time during an impact test.

To generate the frequency response function of the workpiece 12, the computer 32 first records the impact force generated during an impact test (i.e., by measuring the output of the load cell 22) as well as the resulting frequency response of the workpiece 12 to the impact test (i.e., by measuring the output of the accelerometer 18). An example of this information which is recorded by the computer 32 is represented in the graphs shown in FIGS. 3(A) and 3(B). Because the load cell 22 generates an output which is proportional to the force applied to the workpiece 12 by the impact hammer 20, the computer 32 is able to normalize the output of the accelerometer 18 so as to minimize the variation of the output due to variation in the force applied by the impact hammer 20.

Figure 3C:
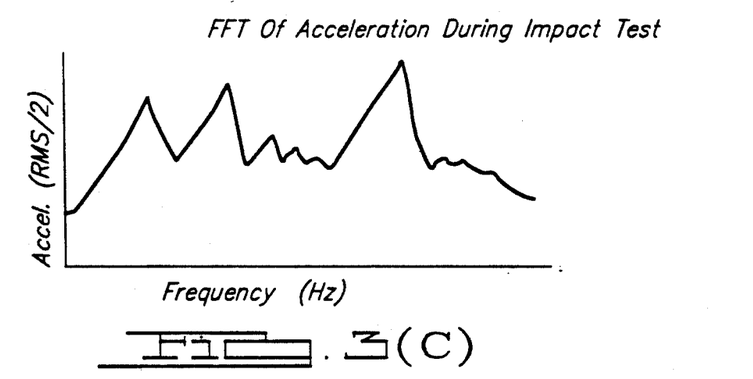
FIG. 3(C) illustrates a graph generated by the apparatus shown in FIG. 1 depicting the fast fourier transform of the output of the accelerometer during an impact test.
Figure 3D:
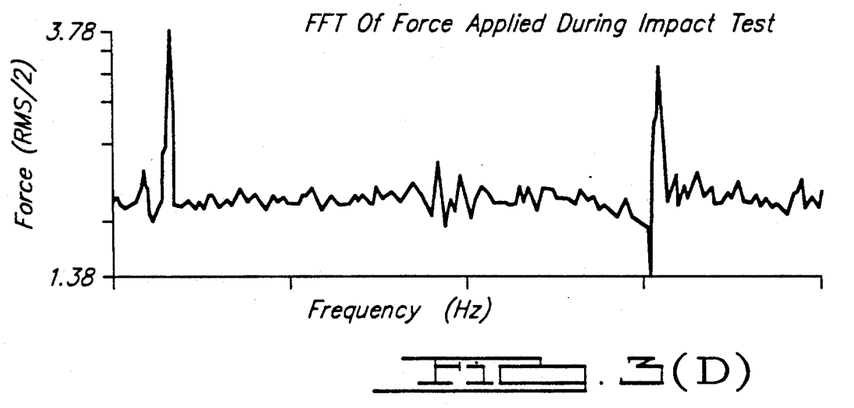
FIG. 3(D) illustrates a graph generated by the apparatus shown in FIG. 1 depicting the fast fourier transform of the force applied to the workpiece during an impact test.

The computer 32 then calculates both the fast fourier transform of the acceleration of the workpiece 12 from the output of the accelerometer 18 as well as the fast fourier transform of the force applied to the workpiece 12 during the impact test from the output of the load cell 22. An example of the fast fourier transform of the output of the accelerometer 18 is shown in FIG. 3(C), while an example of the fast fourier transform of the output of the load cell 22 is shown in FIG. 3(D). A variety of methods may be used for calculating the fast fourier transforms of outputs from the accelerometer 18 and the load cell 22. The preferred method of the present invention uses the fast fourier transform calculation methods executed using P-DAAS software available from PEMTECH of Cincinnati, Ohio. However, other suitable methods may be used.

Once the computer 32 determines the fast fourier transform using both the output of the accelerometer 18 and the load cell 22 during the impact test the computer 32 determines the frequency response function of the workpiece 12. The frequency response function is a representation of the vibrational characteristics of the workpiece 12 as a function of the frequency of the force applied to the workpiece 12. The frequency response function can be mathematically represented as follows:

$$H(\omega) = \frac{X(\omega)}{F(\omega)}$$

where
  $H(\omega)$ is the frequency response function;
  $F(\omega)$ is the frequency of the force applied to the workpiece 12;
  $X(\omega)$ is the response of the workpiece 12 to the force which is applied; and
  $\omega$ is frequency.

Figure 3E:
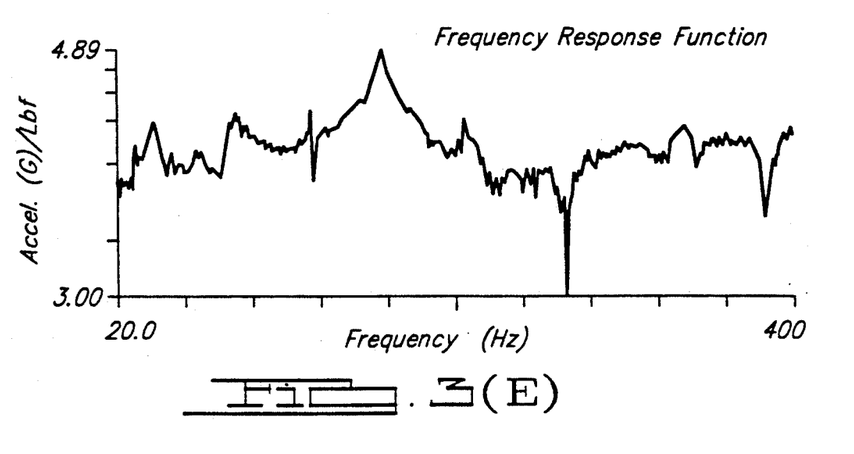
FIG. 3(E) illustrates a graph generated by the apparatus shown in FIG. 1 of the frequency response function of the workpiece after a single impact during an impact test.
Figure 3F:
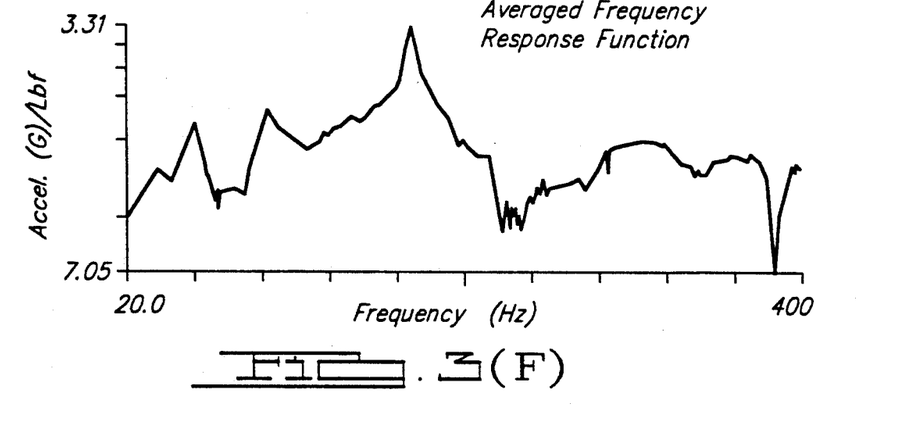
FIG. 3(F) illustrates a graph generated by the apparatus shown in FIG. 1 of the averaged frequency response function of the workpiece after several impact during an impact test.

Graphical representation of the frequency response function for the workpiece 12 are shown in FIGS. 3(E) and 3(F). The frequency response function shown in FIG. 3(E) represent the frequency response function which was generated from a single impact of the workpiece 12 during the impact test, while the frequency response function shown in FIG. 3(F) represents the average frequency response function of the workpiece 12 for several impacts.

It will be appreciated that the frequency response function is independent of the magnitude of the force applied during the impact test and that local maxima of the frequency response function occur at frequencies of dynamic weakness in the workpiece 12. In addition, it will also be appreciated that the local minima of the frequency response function indicate frequencies at which the workpiece 12 has dynamic strength.

2. Determining the Critical Frequency of the Workpiece

Once the computer 32 has determined the frequency response function of the workpiece 12 in the manner described above, the computer 32 then determines the critical resonant frequency of the workpiece 12 as shown in FIG. 2. The computer 32 then uses the critical resonant frequency of the workpiece 12 in the third operation described below to establish the frequency at which the workpiece 12 is to be initially vibrated.

Figure 4A:
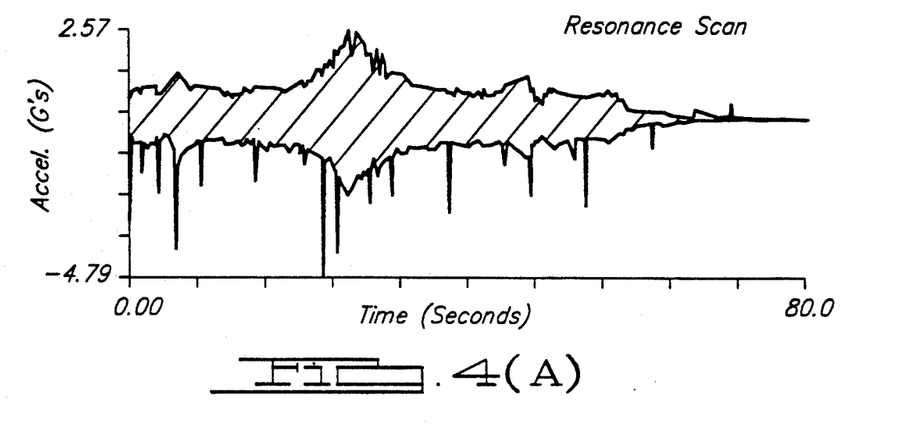
FIG. 4(A) illustrates a graph generated by the apparatus shown in FIG. 1 showing a resonance scan of the workpiece prior to being stress relieved.
Figure 4B:
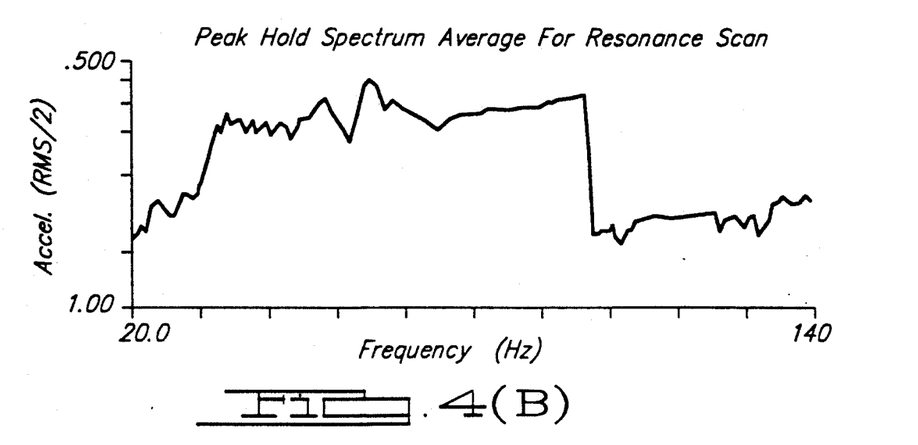
FIG. 4(B) illustrates a graph generated by the apparatus shown in FIG. 1 showing the peak hold spectrum average for the resonant scan of FIG. 4.

To determine the critical resonant frequency of the workpiece 12, the computer 32 causes the exciter 14 to begin vibrating at progressively higher frequencies at a constant rate until reaching a predetermined maximum, as dictated by the mass and geometry of the workpiece, in most cases not to exceed 150 Hz. A fragile, more complex workpiece may require less input force at a higher frequency of vibration. A workpiece of less complex geometry and greater mass may require more input force at a lower frequency of vibration. After this frequency has been reached, the computer 32 causes the frequency of the vibration delivered to the workpiece 12 by the exciter 14 to decrease at a constant rate until the vibration terminates. As this occurs, the computer 32 records the output of the accelerometer as a function of time so as to generate a resonance scan of the workpiece 12. The computer 32 then takes the fast fourier transform of the information used to generate the resonance scan to obtain the peak hold spectrum average for the resonance scan, which summarizes the amplitude of response of the workpiece 12 across a range of vibration inputs. A graphical illustration of the resonance scan depicting output of the accelerometer as a function of time is shown in FIG. 4(A), while a graphical illustration of the peak hold spectrum average depicting the fast fourier transform of the output of the accelerometer as a function of frequency is shown in FIG. 4(B). The maximum peaks of the fast fourier transform, defined as those points of frequency of greatest amplitude within the scanned range, are then compared with those of the averaged frequency response function of the impact test, to determine the critical resonant peak frequency. This is done by choosing the peak on the resonance scan graph which correlates most closely with a peak on the impact test graph. If two peaks on the resonance scan correlate equally to two peaks on the impact test, generally the pair of peaks exhibiting greater relative amplitude is designated the critical resonant peak frequency.

3. Varying the Frequency at Which the Workpiece is Vibrated

Once the fast fourier transform of the output of the accelerometer 48 has been determined as a function of the frequency of the vibration caused by the exciter 14, the computer 32 causes the exciter 14 to vibrate at a frequency which is slightly above or below the critical resonant frequency within a range of 30 to 150 Hz. This operation represents the third operation shown in FIG. 2. Typically, the initial frequency at which the exciter 14 vibrates the workpiece 12 will be within 2.5 Hz of the critical resonant frequency.

As stress is removed from the workpiece 12, the critical resonance frequency of the workpiece 12 may change. The computer 32 monitors any change by repeatedly calculating the fast fourier transform of the output of the accelerometer 18 and then determining the frequency at which the magnitude of the output of the accelerometer 18 is the greatest within the 30 to 150 Hz range. As the critical resonant frequency changes, the computer 32 changes the frequency at which the exciter 14 vibrates the workpiece 12 so as to maintain the frequency of the vibration applied to the workpiece 12 within 2.5 Hz of the critical resonant frequency.

Figure 5:
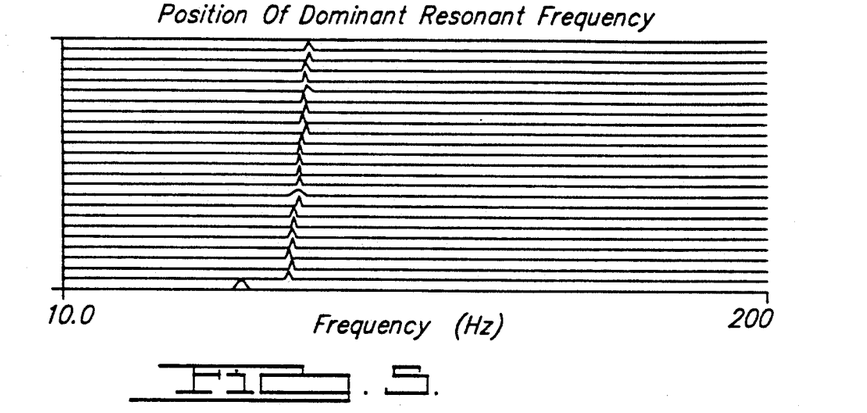
FIG. 5 illustrates a graph generated by the apparatus shown in FIG. 1 showing the change in the dominant resonant frequency of the workpiece is undergoing stress relief.

The computer 32 also monitors the rate of change of the critical resonant frequency as the workpiece 12 is vibrated. An example of this rate of change of the critical resonant frequency is illustrated in FIG. 5, which represents a waterfall chart of the output of the accelerometer 18 as a function of the frequency of vibration applied to the workpiece 12 at various times during vibration. When the computer 32 determines that the critical resonant frequency of the workpiece 12 has remained relatively constant, for example, when the critical resonant peaks line up on the waterfall graph successively, showing less than a one half (0.5) Hz change in frequency over at least four scans, the computer 32 terminates further vibration of the workpiece 12.

4. Comparing the Final Frequency Response of the Workpiece With the Initial Frequency Response of the Workpiece The computer 32 is also able to compare the frequency response of the workpiece 12 after vibration of the workpiece 12 has terminated with the frequency response of the workpiece 12 before vibration was initiated. This is represented as the last step in FIG. 2 and permits a visual inspection of the changes in the frequency response of the workpiece 12 as a result of the force applied to the workpiece 12.

To compare the changes in the frequency response of the workpiece 12 as a result of the force applied to the workpiece 12, the computer 32 records the output of the accelerometer 18 and the load cell 22 during a second impact test, or series of impact tests, performed on the workpiece 12 after the workpiece 12 has been vibrated. The computer 32 then generates a second frequency response function of the workpiece 12 which is overlaid with the frequency response function of the workpiece 12 which was determined before the workpiece 12 was vibrated. An illustration of such an overlay of the frequency response function is shown in FIG. 7, the use of which permits changes in the dynamic stiffness and modal behavior of the workpiece to be determined. The computer 32 also generates an overlay of the peak hold spectrum average of the workpiece 12 after the workpiece 12 has been vibrated with the peak hold spectrum average before the workpiece 12 was vibrated. Such a comparison is shown in FIG. 7 to show any changes in the frequency and amplitude of the vibrational response, or modal, behavior of the workpiece 12.

The operation of the apparatus 12 of the present invention will now be described. The workpiece 12 is initially disposed on a resilient material (not shown), such as rubber or the like, thereby allowing the workpiece 12 to respond freely when vibrated by the exciter 14. Alternately, the workpiece 12 may be secured to a worktable, with the table similarly isolated by itself being disposed on a resilient material. For a workpiece too large to isolate practically, no isolation may be employed, although in this case the period required to vibrate and stabilize the workpiece 12 can be expected to take longer than if the workpiece 12 were isolated.

Next, the impact hammer 20 is used to exert a force on the workpiece 12, the magnitude of which is recorded by the load cell 22. The output of the load cell 22 is delivered to the computer 32 through the multi-channel signal conditioning unit as well as the analog-to-digital converter. Simultaneously, the accelerometer 18 also records the force of the impact, and its output is conveyed to the computer 32 through the multi-channel signal conditioning circuit as well as the analog-to-digital converter. Preferably, the impact hammer 20 is used to strike the workpiece 12 four times in this manner during the impact test to generate an averaged frequency response function, which will later be used for comparison with the workpiece's frequency response function after vibrational treatment. The apparatus 32 then may display the results of the impact test by generally graphs similar to those which are shown in FIGS. 3(A)-3(F) either on the monitor 26 or by the printer 28, which present graphically the data required to compute the frequency response functions for the subsequent steps of the operation.

Once the impact test has been conducted, the computer 32 then causes the exciter 14 to perform a controlled ramp-up of vibrational amplitude at a constant rate from zero frequency to a predetermined maximum frequency and a controlled ramp-down at a constant rate to zero frequency to enable the computer 32 to examine the resonance frequencies of the workpiece 12. After the resonance scan of the workpiece 12 is performed as described above, the apparatus 10 generates a visual display of the resonance scan as well as the peak hold spectrum average. These visual displays may appear on the monitor 26 or printed in hard copy by the printer 28 and are similar to FIGS. 4(A) and 4(B), respectively.

After the resonant scan has been conducted, the apparatus 10 begins to vibrate the workpiece 12 at a frequency which is near the critical resonant frequency (e.g., within 2.5 Hz) of the critical resonant frequency of the workpiece 12. A check is made to confirm that a peak is present in the frequency response function illustrated in FIG. 3(F) at or substantially near the same frequency in the peak hold spectrum average shown in FIG. 4(B). The maximum peaks of the fast fourier transform, defined as those points of frequency of greatest amplitude within the scanned range, compared with those of the averaged frequency response function of the impact test, determine the critical resonant peak frequency. This is done by choosing the peak on the resonance scan graph which correlates most closely with a peak on the impact test graph. If two peaks on the resonance scan correlate equally to two peaks on the impact test, generally the pair of peaks exhibiting greater relative amplitude is designated the critical resonant peak frequency. As the critical resonant peak frequency of the workpiece 12 changes, the apparatus 10 changes the frequency at which the exciter 14 vibrates the workpiece 12 so as to maintain the frequency at which the workpiece 12 is vibrated relatively close to the critical resonance frequency. At the same time, the apparatus 10 provides a visual indication of the manner in which the critical resonant frequency changes which is similar to FIG. 5 either by the monitor 26 or by the printer 28.

Figure 6A:
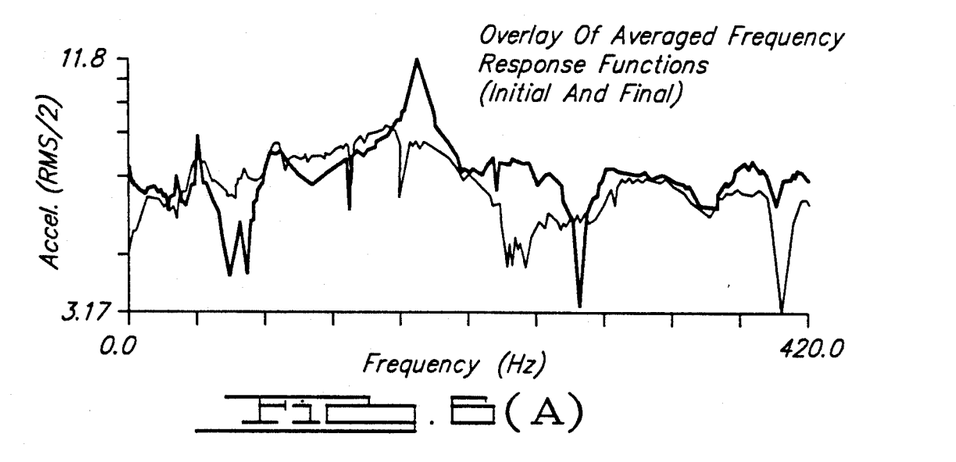
FIG. 6(A) illustrates a graph generated by the apparatus shown in FIG. 1 showing an overlay of the frequency response function of the workpiece before and after undergoing stress relief.
Figure 6B:
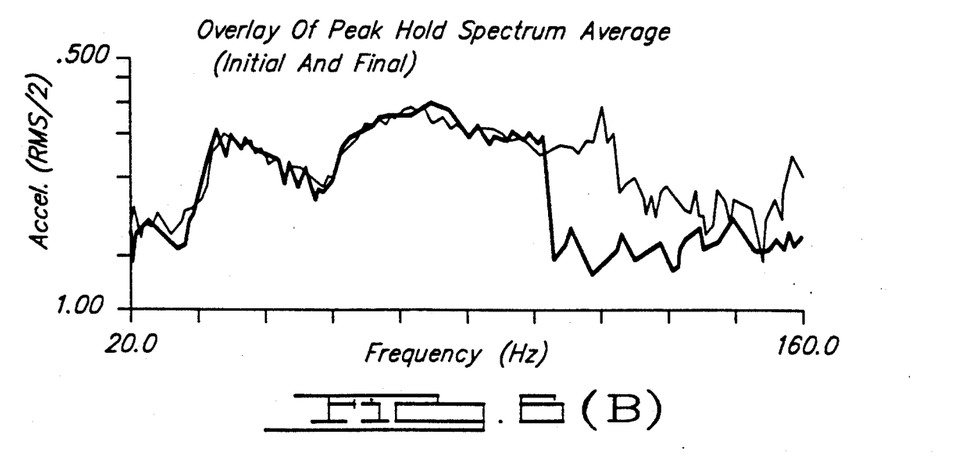
FIG. 6(B) illustrates a graph generated by the apparatus shown in FIG. 1 showing an overlay of the peak hold spectrum average of the workpiece before and after undergoing stress relief.

When the critical resonant frequency remains relatively stable for a period of time, the apparatus 10 terminates vibration of workpiece 12 and a second impact test is performed on the workpiece 12. The apparatus 10 then conducts a second resonance scan to determine the peak hold spectrum average of the workpiece 12 exactly duplicating the vibrational range of the initial resonance scan. The apparatus 10 then may generate a visual display comparing the first resonance scan with the second resonance scan, the first peak hold spectrum average with the second peak hold spectrum average and the first frequency response function (impact test) with the second. This visual display may be generated by the monitor 26 or by the printer 28 and may be similar to the graphs which are illustrated in FIG. 6(A) and FIG. 6(B).

It will also be appreciated that the apparatus and method disclosed in this invention may be employed to confirm change (or lack thereof) in modal behavior of, and therefore relief of residual stresses in, workpieces treated by other vibrational or non-vibrational residual stress relief methods. For that purpose, all steps in the procedure are followed, except for the extended vibrational dwell period (the third operation shown in FIG. 2). For example, before and after heat treating, an impact test and resonance scan may be undertaken on a workpiece to show changes in modal behavior of the workpiece caused by relief or redistribution of residual stresses, or introduction of residual stresses caused by improper heat treatment practice.

In addition, the application of modal analysis and fast fourier transform techniques, though heretofore limited to predictive maintenance programs, can now be applied through this invention for the purpose of preventative maintenance. For example, a die-cast mold for casting aluminum wheels which has been relieved of residual stresses by the method and/or apparatus of this invention may be evaluated at a later date, after use which may introduce residual stresses. In order to assess any changes in modal behavior which may indicate a build up of residual stresses, the data and graphs generated by the post-treatment impact tests and resonance scan are compared with impact tests and a resonance scan performed on the workpiece after it has been in use. If there is essentially no change in modal behavior of the mold, as indicated by the comparative frequency response functions and peak hold spectrum averages, no further treatment beyond the impact test and resonance scan is required at that time. If change is substantial, as indicated by comparing the respective impact test and resonance scan graphs, then the mold is stabilized by proceeding through the remaining steps of the full treatment process described in this invention, and is ready to go back into service. In terms of workpiece maintenance and procedure, the present invention enables one skilled in the art to combine the predictive with the preventative, effectively extending the work life of workpieces, through routine modal analysis using the methods disclosed by this invention, thereby allowing workpieces to wear naturally rather than fail prematurely. Also, workpieces may be kept in working condition longer by removing residual stresses incrementally on a routine basis, and remain repairable when otherwise they may fail so completely as to become unsalvageable and/or damage adjacent tooling.

Similarly, on workpieces treated for residual stress relief by methods other than disclosed by this invention, an impact test series and resonance scan may be performed after such other treatments, for later comparison with impact tests and resonance scans after use which may introduce residual stresses, to determine the need for stress relief in advance of any dimensional changes, heat checking, or other empirical evidence of residual stress buildup.

The foregoing discussion describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims. For example, during welding, the impact test may be omitted, with reliance on the resonance scan to determine the frequency at which the workpiece is to be vibrated during welding and through the post-welding cooling period frequency at which the workpiece is to be vibrated during welding, until the temperature of the workpiece is sufficiently cooled (e.g., until the temperature of the workpiece is approximately 150° C.) and thereby stabilized.

What is claimed is:

1. An apparatus for relieving residual stresses in a workpiece comprising:
   means for vibrating said workpiece;
   means for detecting movement of said workpiece and generating an output in response thereto; and
   means for repeatedly varying the frequency at which said workpiece is vibrated in response to said output of said means for detecting movement of said workpiece in order to maintain the frequency at which said workpiece is vibrated relatively close to a resonant frequency of said workpiece.

2. The apparatus for relieving residual stresses as set forth in claim 1, wherein said means for detecting include an accelerometer being operable to generate said output, said output of said accelerometer being operable to determine the frequency at which said workpiece is vibrated.

3. The apparatus for relieving residual stresses as set forth in claim 2, wherein said means for varying the frequency at which said workpiece is vibrated is operable to determine the fast fourier transform of the output of said accelerometer.

4. The apparatus for relieving residual stresses as set forth in claim 1, wherein said means for varying the frequency at which said workpiece is vibrated is operable to maintain the frequency at which said workpiece is vibrated relatively close to the critical resonant frequency of said workpiece.

5. The apparatus for relieving residual stresses as set forth in claim 4, wherein the frequency at which said workpiece is vibrated is determined by recursively calculating the fast fourier transform of the acceleration of said workpiece.

6. The apparatus for relieving residual stresses as set forth in claim 1, further comprising an impact hammer which is used for conducting an impact test on said workpiece, said impact hammer including a load cell being operable to generate an output in response to the force applied by said impact hammer during said impact test.

7. The apparatus for relieving residual stresses as set forth in claim 6, wherein said means for varying the frequency of vibration of said workpiece is operable to compensate for variation in the force applied to said workpiece during said impact test upon receipt of said output of said load cell.

8. The apparatus for relieving residual stresses set forth in claims 1, 2, 3, 4, 5, 6 or 7, further comprising means for displaying the change in said residual stresses after said workpiece has been vibrated.

9. An apparatus for reliving residual stresses in a workpiece, said workpiece having a critical resonant frequency which changes as said workpiece is vibrated, said apparatus comprises:
an exciter operable to vibrate said workpiece;
means for detecting movement of said workpiece and generating said critical resonant frequency; and
a control unit operable to repeatedly vary the frequency at which said workpiece is vibrated in response to the changing of the critical resonant frequency of said workpiece in order to maintain the frequency at which said workpiece is vibrated relatively close to the critical resonant frequency of said workpiece.

10. The apparatus for relieving residual stresses as set forth in claim 9, wherein said means for detecting includes an accelerometer mechanically communicating with said workpiece, said accelerometer operable to determine the frequency response of said workpiece in response to vibration of said workpiece.

11. The apparatus for relieving residual stresses as set forth in claim 10, wherein said control unit is operable to determine the fast fourier transform of the output of said accelerometer.

12. The apparatus for relieving residual stresses as set forth in claim 11, wherein said control unit recursively calculates the fast fourier transform of the frequency response of said workpiece.

13. The apparatus for relieving residual stresses as set forth in claim 12, wherein said control unit vibrates said workpiece until the position of said critical resonant frequency stabilizes.

14. The apparatus for relieving stresses as set forth in claim 9, further comprising an impact hammer including a load cell, said impact hammer being in communication with said control unit.

15. The apparatus for relieving residual stresses set forth in claims 9, 10, 11, 12, 13 or 14, further comprising means for displaying the change in said residual stresses of said workpiece after said workpiece has been vibrated.

16. A method of relieving residual stresses in a workpiece comprising the steps of:
attaching an exciter to said workpiece, said exciter being operable to vibrate said workpiece;
attaching an accelerometer to said workpiece, said accelerometer operable to generate an output in response to the vibration of said workpiece;
repeatedly varying the frequency at which said workpiece is vibrated in response to said output of said accelerometer in order to maintain the frequency at which said workpiece is vibrated relatively close to a resonant frequency at said workpiece.

17. The method for relieving residual stresses as set forth in claim 16, further comprising the additional step of determining an initial critical resonant frequency of said workpiece.

18. The method for relieving residual stresses as set forth in claim 17, wherein the step of determining an initial critical frequency comprises the step of energizing said exciter over a test frequency range.

19. The method for relieving residual stresses as set forth in claim 17, wherein the step of varying the frequency of which said workpiece is vibrated comprises the step of determining the frequency at which said workpiece is vibrated through recursive application of fast fourier analysis to recalculate said critical resonant frequency.

20. The method for relieving residual stresses as set forth in claim 19, further comprising the step of terminating the vibration generated by the exciter when the position of said critical resonant frequency of said workpiece stabilizes.

21. The method for relieving residual stresses as set forth in claim 20, further comprising the additional step of normalizing the frequency response of said workpiece during an impact test.

22. The method for relieving residual stresses as set forth in claims 16, 17, 18, 19, 20 or 21, further comprising the additional step of displaying the changes in the residual stresses of said workpiece after said workpiece has been vibrated.

23. An apparatus for verifying changes in the modal behavior of a workpiece caused by the relief of residual stresses, said apparatus comprising:
means for vibrating said workpiece;
means for detecting movement of said workpiece and generating an output in response thereto;
means for repeatedly varying the frequency at which said workpiece is vibrated in response to said output of said means for detecting movement of said workpiece in order to maintain the frequency at which said workpiece is vibrated relatively close to a resonant frequency of said workpiece; and
means for determining movement of the critical resonance frequency of said workpiece as a result of said change in the modal behavior of said workpiece, said means for determining movement of the critical resonant frequency of said workpiece being operable to determine the fast fourier transform of said output of said means for detecting movement of said workpiece.

24. The apparatus for verifying changes in the modal behavior of a workpiece as set forth in claim 23, wherein said means for detecting includes an accelerometer being operable to determine the frequency at which said workpiece is vibrated.

25. The apparatus for verifying changes in the modal behavior of a workpiece as set forth in claim 24, further comprising an impact hammer which is used for conducting an impact test on said workpiece, said impact hammer including a load cell being operable to generate an output in response to the force applied by said impact hammer during said impact test.

26. The apparatus for verifying changes in the modal behavior of a workpiece as set forth in claim 25, wherein said means for determining movement of the critical resonance frequency of said workpiece is operable to compensate for variation in the force applied to said workpiece during said impact test upon receipt of said output of said load cell.

27. A method for verifying the change in the modal behavior of a workpiece caused by the relief of residual stresses, said method comprising;
  calculating the fast fourier transform of the frequency response of said workpiece to vibration prior to subjecting said workpiece to residual stress relief;
  subjecting said workpiece to residual stress relief by:
  attaching an exciter to said workpiece, said exciter being operable to vibrate said workpiece;
  attaching an accelerometer to said workpiece, said accelerometer operable to generate an output in response to the vibration of said workpiece;
  repeatedly varying the frequency at which said workpiece is vibrated in response to said output of said accelerometer in order to maintain the frequency at which said workpiece is vibrated relatively close to a resonant frequency of said workpiece;
  calculating the fast fourier transform of the frequency response of said workpiece to vibration subsequent to subjecting said workpiece to stress relief; and
  comparing the fast fourier transformer of the frequency response of said workpiece prior to stress relief to the fast fourier transform of the frequency response of said workpiece subsequent to residual stress relief,
  whereby the change in modal behavior of said workpiece as a result of said stress relief may be verified.

28. The method for verifying the change in the modal behavior of a workpiece as set forth in claim 27, further comprising the additional step of determining the initial critical resonant frequency of said workpiece.

29. The method for verifying the change in the modal behavior of a workpiece as forth in claim 28, wherein the step of determining the frequency response of said workpiece to vibration prior to subjecting said workpiece to residual stress relief comprises the step of energizing an exciter over a test frequency range.

* * * * *